(12) United States Patent
Hosoi

(10) Patent No.: US 7,874,676 B2
(45) Date of Patent: Jan. 25, 2011

(54) VISION TESTER

(75) Inventor: Yoshinobu Hosoi, Gamogori (JP)

(73) Assignee: Nidek Co., Ltd., Gamagori (JP)

( * ) Notice: Subject to any disclaimer, the term of this patent is extended or adjusted under 35 U.S.C. 154(b) by 448 days.

(21) Appl. No.: 11/989,833

(22) PCT Filed: Sep. 1, 2006

(86) PCT No.: PCT/JP2006/317313

§ 371 (c)(1),
(2), (4) Date: Feb. 1, 2008

(87) PCT Pub. No.: WO2007/026866

PCT Pub. Date: Mar. 8, 2007

(65) Prior Publication Data

US 2010/0157249 A1    Jun. 24, 2010

(30) Foreign Application Priority Data

Sep. 2, 2005    (JP) .............................. 2005-254623

(51) Int. Cl.
    *A61B 3/02* (2006.01)
(52) U.S. Cl. ...................................... 351/235; 351/239
(58) Field of Classification Search .......... 351/200–246
    See application file for complete search history.

(56) References Cited

U.S. PATENT DOCUMENTS

| | | | | |
|---|---|---|---|---|
| 3,891,311 | A | * | 6/1975 | Fletcher et al. ............. 351/245 |
| 4,844,607 | A | * | 7/1989 | Andera et al. ................ 351/243 |
| 5,812,241 | A | | 9/1998 | Doms et al. .................. 351/217 |
| 5,929,971 | A | | 7/1999 | Hosoi et al. .................. 351/237 |
| 6,923,541 | B2 | | 8/2005 | Hosoi et al. .................. 351/235 |
| 2003/0081175 | A1 | * | 5/2003 | Hosoi et al. .................. 351/222 |
| 2004/0130679 | A1 | | 7/2004 | Hosoi .......................... 351/222 |
| 2007/0052924 | A1 | * | 3/2007 | Nozawa et al. ............... 351/205 |

FOREIGN PATENT DOCUMENTS

| | | |
|---|---|---|
| DE | 296 00 127 U1 | 4/1996 |
| EP | 1 308 123 A2 | 5/2003 |
| EP | 1 442 697 A1 | 8/2004 |
| JP | A-64-20824 | 1/1989 |
| JP | U-05-48902 | 6/1993 |
| JP | A-09-505209 | 5/1997 |
| JP | A-10-014872 | 1/1998 |
| JP | A-2001-346762 | 12/2001 |
| JP | A-2003-135397 | 5/2003 |
| JP | A-2003-135398 | 5/2003 |
| JP | A-2004-208705 | 7/2004 |

* cited by examiner

*Primary Examiner*—Mohammed Hasan
(74) *Attorney, Agent, or Firm*—Oliff & Berridge, PLC

(57) ABSTRACT

A subjective vision tester includes a pair of right and left lens chamber units (2) each having a test window (4), a first lens disk (11-14) provided with an aperture and a plurality of optical elements (110, 120, 130, 140) and placed in a position closer to an examinee's eye (E) within the each lens chamber unit, and a second lens disk (15, 16) provided with an aperture (151, 161) and a plurality of optical elements (150, 160) and placed in a position farther from the examinee's eye than the first lens disk within the lens chamber unit. The first lens disk and the second lens disk are equal in diameter. The diameter of the diameter of the aperture in the second lens disk is larger than each optical element in the first lens disk.

7 Claims, 3 Drawing Sheets

FIG.3

| | 1 | 2 | 3 | 4 | 5 | 6 | 7 | 8 | 9 | 10 | 11 | 12 |
|---|---|---|---|---|---|---|---|---|---|---|---|---|
| H-SPH | 1 | -3.00 | -6.00 | -9.00 | -12.00 | -15.00 | -18.00 | 3.00 | 6.00 | 9.00 | 12.00 | 15.00 |
| L-SPH | 0 | -0.25 | -0.50 | -0.75 | -1.00 | 0.25 | 0.50 | 0.75 | 1.00 | 1.25 | 1.50 | 1.75 |
| H-CYL | 0 | -1.50 | -3.00 | -4.50 | -6.00 | -7.50 | | | | | | |
| L-CYL | 0 | -0.25 | -0.50 | -0.75 | -1.00 | -1.25 | | | | | | |
| AUX1 | 0 | 0.12 | R/G | 6/10Δ | ±0.5XC | P135 | P45 | 0.12+P135 | 0.12+P45 | MR | PH | BL |
| AUX2 | 0 | RP | ±0.25XC | ±0.5XC | ±0.25AXC | 10.00 | -10.00 | PD | | | | |

VISION TESTER

TECHNICAL FIELD

The present invention relates to a vision tester (optometer) for subjectively testing (measuring) refractive power of an examinee's eye.

BACKGROUND ART

There is a vision tester that includes a main unit called Phoropter for disposing optical elements such as sphere lenses and cylinder lenses in front of the eye(s) of an examinee. The vision tester is arranged to present an optotype forward at a predetermined test distance to the examinee who views it through the optical elements disposed in front of the eye(s) for a subjective test (measurement) of refractive power and others of the examinee's eye(s).

In such vision tester, a visual field viewable through the optical elements disposed in a test window of the main unit is narrow. This would be likely to cause accommodation interference during a test. For this reason, there has been proposed an apparatus in which the test window and each optical element have larger diameters to widen the visual field in order to restrain the accommodation interference.

When each optical element has a larger diameter, a lens disk rotatably placed in the main unit to hold a plurality of such optical elements would also be increased in diameter, resulting in an increase in size of the main unit.

DISCLOSURE OF INVENTION

Problems to be Solved by the Invention

The present invention has a purpose to provide a vision tester capable of restraining accommodation interference without needing an increase in size of the apparatus, in particular, capable of restraining accommodation interference in a test using a sphere lens and a cylinder lens.

Means for Solving the Problems

To achieve the above purpose, the present invention is characterized in the following configurations.

A subjective vision tester of the present invention is characterized by including: a pair of right and left lens chamber units each having a test window; a first lens disk provided with an aperture and a plurality of optical elements and placed in a position closer to an examinee's eye within each lens chamber unit; and a second lens disk provided with an aperture and a plurality of optical elements and placed in a position farther from the examinee's eye than the first lens disk within the lens chamber unit; wherein the first lens disk and the second lens disk are equal in diameter, and the aperture in the second lens disk has a larger diameter than each optical element in the first lens disk.

In the above vision tester, preferably, the diameter of each optical element in the first lens disk is equal to the diameter of each optical element in the second lens disk.

Further, it may be arranged such that the first lens disk includes a sphere lens disk provided with a sphere lens and a cylinder lens disk provided with a cylinder lens, and the second lens disk includes an auxiliary lens disk provided with an auxiliary lens.

Preferably, the diameter of the aperture in the second lens disk is determined to provide a viewing angle of 40° or more of the examinee's eye.

Furthermore, preferably, the second lens disk includes a plurality of disks, and the diameter of the aperture in the second lens disk placed farthest from the examinee's eye is determined to provide a viewing angle of 40° or more of the examinee's eye.

BRIEF DESCRIPTION OF DRAWINGS

FIG. 3 is a table showing arrangements of optical elements in lens disks.

EXPLANATION OF REFERENCE CODES

Figure 1:
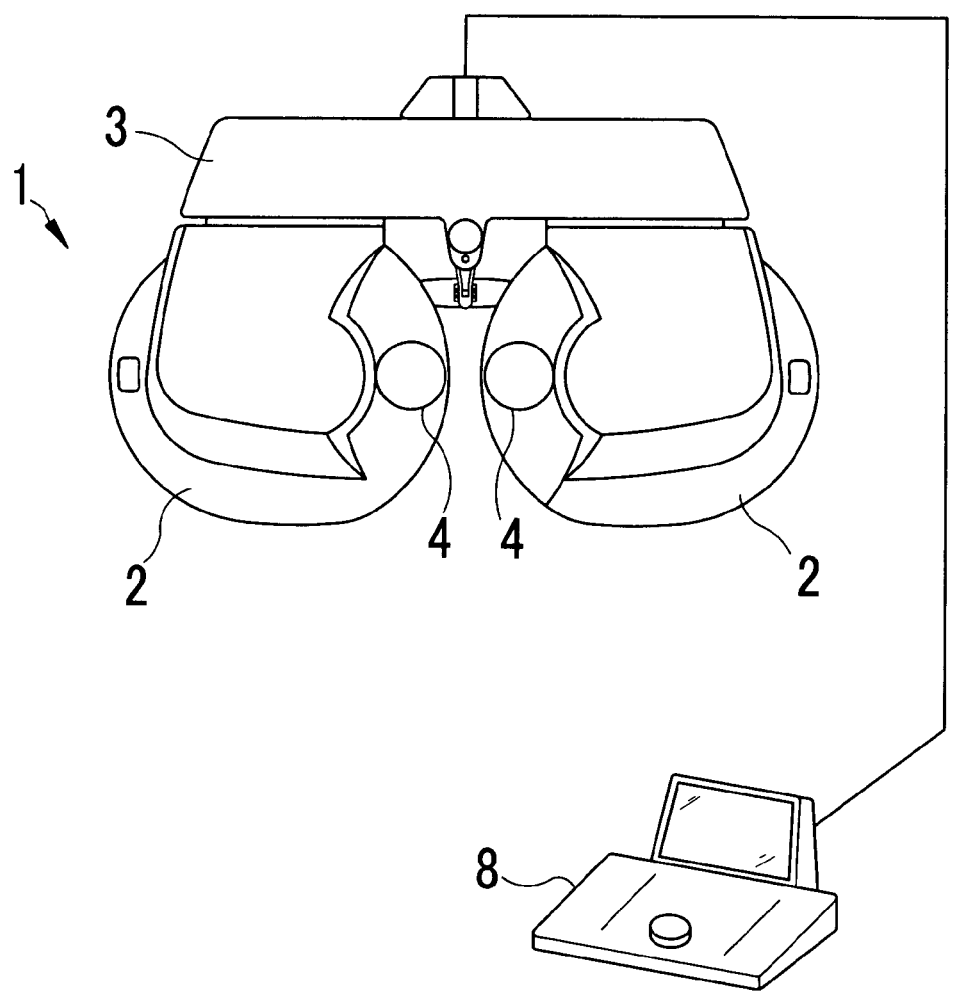
FIG. 1 is a schematic perspective view of a vision tester of a preferred embodiment of the present invention.

1 Main unit
2 Lens chamber unit
3 Support unit
4 Test window
8 Control part
11 High-power sphere lens disk
12 Low-power sphere lens disk
13 High-power cylinder lens disk
14 Low-power cylinder lens disk
15 First auxiliary lens disk
16 Second auxiliary lens disk
110, 120 Sphere lens
130, 140 Cylinder lens
150, 160 Auxiliary lens
151, 161 Aperture
α Viewing angle

BEST MODE FOR CARRYING OUT THE INVENTION

A detailed description of a preferred embodiment of the present invention will now be given referring to the accompanying drawings.

FIG. 1 is a schematic perspective view of a subjective vision tester of the embodiment of the present invention, seen from an examiner's side. A main unit (phoropter) 1 of the vision tester includes a pair of symmetrical right-and-left lens chamber units 2 and a support unit 3 which supports the lens chamber units 2 in a hanging manner. In each of the lens chamber units 2, a plurality of lens disks is rotatably mounted, each of the lens disks holding optical elements such as sphere lenses and cylinder lenses in a circle. One of the optical elements in each lens disk is selectively disposed in a test window 4 of each lens chamber unit 2. The support unit 3 is provided with a sliding mechanism for adjusting the interval between the lens chamber units 2 to change the interval between the test windows 4 according to the inter pupillary distance between the eyes of an examinee and a convergence mechanism for adjusting a convergence angle of the lens chamber units 2 (the structure of each mechanism has been well known and thus its explanation is not repeated here).

A control part (controller) 8 of the vision tester is used to enter a signal or the like for selecting the optical elements to be disposed in each test window 4.

Figure 2:
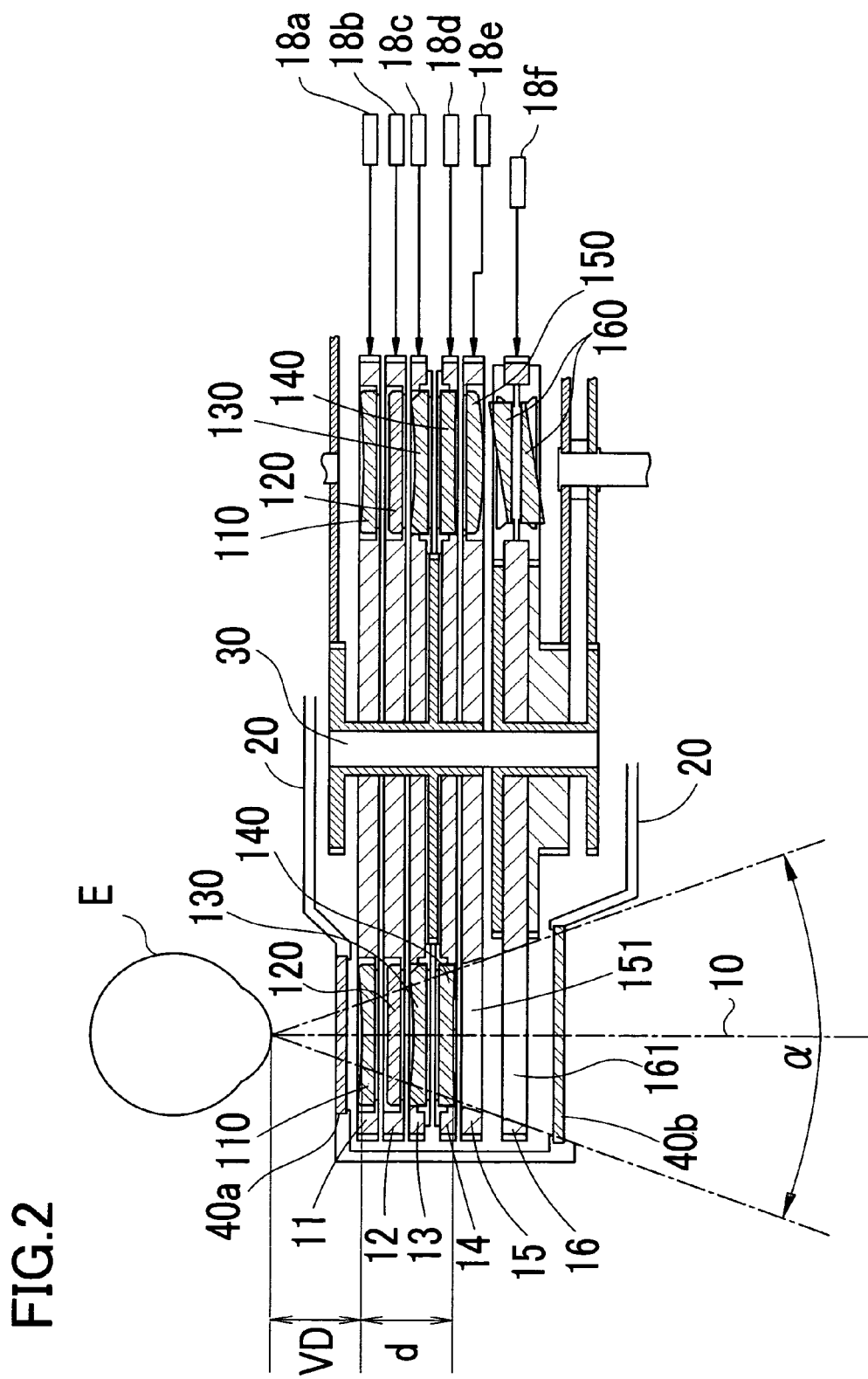
FIG. 2 is a partial sectional view of a lens chamber unit for left eye, seen from above.

FIG. 2 is a partial sectional view of the lens chamber unit 2 for left eye, seen from above. A cover 20 of the lens chamber unit 2 houses a plurality of lens disks arranged to be rotatable around a shaft 30, each disk being provided with an aperture (or a lens of 0D) and a plurality of optical elements. In the present embodiment, six lens disks, that is, a high-power sphere lens disk 11, a low-power sphere lens disk 12, a high-power cylinder lens disk 13, a low-power cylinder lens disk 14, a first auxiliary lens disk 15, and a second auxiliary lens disk 16 are arranged in the order of nearest to farthest relative to an examinee's eye E. The lens disk 11 is rotated by a motor 18a. The lens disk 12 is rotated by a motor 18b. The lens disk 13 is rotated by a motor 18c. The lens disk 14 is rotated by a motor 18d. The lens disk 15 is rotated by a motor 18e. The lens disk 16 is rotated by a motor 18f. In this way, the optical elements are selectively disposed on a measurement optical axis 10 passing almost the center of the test window 4.

On the side of the test window 4 of the lens chamber unit 2 closer to the examinee (examinee's eye E), a protective glass 40a is mounted. On the other side of the test window 4 closer to the examiner, a protective glass 40b is mounted.

FIG. 3 is a table showing arrangements of the optical elements in the lens disks 11 to 16. The lens disks 11 to 16 are equal in diameter, which is 110 mm in the present embodiment. In FIG. 3, "0" represents the aperture (or a 0 D lens). In the following description, D indicates diopter representing refractive power.

In the present embodiment, the high-power sphere lens disk (H-SPH) 11 holds eleven high-power sphere lenses 110 (−18D, −15D, −12D, −9D, −6D, −3D, +3D, +6D, +9D, +12D, +15D), and the low-power sphere lens disk (L-SPH) 12 holds eleven low-power sphere lenses 120 (−1D, −0.75D, −0.5D, −0.25D, +0.25D, +0.5D, +0.75D, +1D, +1.25D, +1.5D, +1.75D). The sphere lenses 110 and 120 in the present embodiment have a diameter of 20 mm (19 mm in effective diameter).

In the present embodiment, the high-power cylinder lens disk (H-CYL) 13 holds five high power cylinder lenses 130 (−7.5D, −6D, −4.5D, −3D, −1.5D) and the low-power cylinder lens disk (L-CYL) 14 holds five low-power cylinder lenses 140 (−1.25D, −1D, −0.75D, −0.5D, −0.25D). The cylinder lenses 130 and 140 are rotatable around the optical axis 10 (the structure or the like of a rotation mechanism has been well known and the explanation thereof will not be repeated here). The cylinder lenses 130 and 140 in the present embodiment have a diameter of 20 mm (19 mm in effective diameter).

In the present embodiment, the first auxiliary lens disk (AUX1) 15 holds auxiliary lenses 150 including a sphere lens of +0.12D (0.12), a red filter and a green filter (R/G), a dispersion prism (6/10Δ), a cross cylinder lens of ±0.5D (±0.5XC), two polarizing plates (P135, P45), two polarizing plates of +0.12D (0.12+P135, 0.12+P45), a Maddox lens (MR), a pinhole (PH), and a blind plate (BL). The cross cylinder lens is rotatable around the optical axis 10 (the structure or the like of a rotation mechanism has been well known and the explanation thereof will not be repeated here). The auxiliary lenses 150 in the present embodiment have a diameter of 20 mm (19 mm in effective diameter).

It is to be noted that the diameter of an aperture 151 formed in the lens disk 15 is determined to be larger than the diameter of each optical element in each lens disk 11 to 14 in order to provide a wider viewing angle α of the examinee's eye E as compared with a conventional one. In the present embodiment, the aperture 151 has a diameter of 20.5 mm on the side closer to the examinee and a diameter of 22 mm on the side closer to the examiner.

In the present embodiment, the second auxiliary lens disk (AUX2) 16 holds auxiliary lenses 160 including a rotary prism (RP), a cross cylinder lens of ±0.25D (±0.25XC), a cross cylinder lens of ±0.5D (±0.5 XC), an auto-cross cylinder lens of ±0.25D (±0.25 AXC), a sphere lens of +10D (10.00), a sphere lens of −10D (−10.00), and a flat lens (PD) with a mark for adjustment of interpupillary distance. The rotary prism, cross cylinder lens, and auto-cross cylinder lens are rotatable around the optical axis 10 (the structure or the like of a rotation mechanism has been well known and the explanation thereof will not be repeated here). The auxiliary lenses 160 in the present embodiment have a diameter of 20 mm (19 mm in effective diameter).

It is to be noted that the diameter of an aperture 161 formed in the lens disk 16 is determined to be larger than the diameter of each optical element in each lens disk 11 to 14 in order to provide a wider viewing angle α of the examinee's eye E as compared with a conventional one. In the present embodiment, the aperture 161 is larger in diameter than the aperture 151. In the present embodiment, the aperture 161 has a diameter of 22.5 mm on the side closer to the examinee and a diameter of 25.5 mm on the side closer to the examiner.

In the present embodiment, furthermore, the diameter of the protective glass 40a is slightly larger than the diameter of the optical element (the sphere lens 110) in the lens disk placed closest to the examinee's eye E and the diameter of the protective glass 40b is slightly larger than the diameter of the aperture (the aperture 161) of the lens disk placed farthest from the examinee's eye E.

The reason why the apertures 151 and 161 are different in diameter and also the diameters of each of the apertures 151 and 161 on the side closer to the examinee and on the side closer to the examiner are different from each other is to prevent any components (for example, parts other than the optical elements disposed in the test window 4) from being visible to the examiner when the apertures 151 and 161 are disposed in the test window 4. Of course, the apertures 151 and 161 may be equal in diameter. The diameters of each of the apertures 151 and 161 on the side closer to the examinee and the side closer to the examiner may be equal to each other.

In the present embodiment, it is arranged such that the viewing angle α of the examinee's eye E is 40° in a standard test using sphere lenses and cylinder lenses without using auxiliary lenses. Accordingly, the sphere lens disk and the cylinder lens disk used in the standard test are placed closer to the examinee while the auxiliary lens disks used in a test which is less frequently conducted such as a prism test are placed closer to the examiner.

For the test, the examinee's eye E is positioned so that the distance VD between a corneal apex of the examinee's eye E and the optical element (the sphere lens 110) in the lens disk placed closest to the examinee's eye E is a predetermined distance (generally, VD is 12 mm in Japan). The viewing angle α of the examinee's eye E is determined based on the effective diameter of the optical element in the lens disk placed farthest from the examinee's eye E and a distance d between the optical element in the lens disk placed closest to the examinee's eye E and the optical element in the lens disk placed farthest from the examinee's eye E. In the case of the standard test using the sphere lenses and the cylinder lenses, the optical element closest to the examinee's eye E is the sphere lens 110 in the lens disk 11 and the optical element farthest from the examinee's eye E is the cylinder lens 140 in the lens disk 14. In the case where the effective diameter of the cylinder lens 140 is 19 mm and the distance d is 12.4 mm, the viewing angle α is reliably given as 40° (which can be calculated as a trigonometrical function). Furthermore, the viewing angle α of 40° is provided reliably based on that the apertures 151 and 161 have a larger diameter than the diameter (effective diameter) of the cylinder lens 140 and the protective glass 40b has a larger diameter than the diameter of the aperture 161.

In this way, in the present embodiment, the diameters of the apertures of the lens disks 15 and 16 placed farther from the examinee's eye E are larger than the diameters of the optical elements in the lens disks 11 to 14 placed closer to the examinee's eye E, so that a desired viewing angle α (40° in the present embodiment) can be provided. In the test using the auxiliary lenses, the desired viewing angle α cannot be provided; however, this test is less frequently conducted and thus a serious problem is unlikely to occur.

In the present embodiment, the viewing angle of the examinee's eye E is given as 40° in the standard test, but it is not limited thereto. Utilizing the technical concept of the present invention can provide the viewing angle of 40° or more of the examinee's eye E.

The invention claimed is:

1. A subjective vision tester including:
a pair of right and left lens chamber units each having a test window;
first lens disks each provided with an aperture and optical elements and placed in a position closer to an examinee's eye within each lens chamber unit, the first lens disks including a sphere lens disk provided with an aperture and sphere lenses, and a cylinder lens disk provided with an aperture and cylinder lenses;
second lens disks each provided with an aperture and optical elements and placed in a position farther from the examinee's eye than the first lens disks within each lens chamber unit, the second lens disks including a first auxiliary lens disk provided with an aperture and auxiliary lenses and a second auxiliary lens disk provided with an aperture and auxiliary lenses;
wherein the first lens disks and the second lens disks are almost equal in diameter,
each optical element in the first lens disks and each optical element in the second lens disks are almost equal in diameter,
the diameter of each optical element and each aperture in the first lens disks is determined to provide a viewing angle of the examinee's eye of 40° or more when each of the optical elements and the apertures in the first lens disks is disposed in the test window,
the diameter of each aperture in the second lens disks is determined to be larger than the diameter of each optical element in the first lens disks and provide the viewing angle of 40° or more when each aperture in the second lens disks is disposed in the test window, and
the diameter of each optical element in the second lens disks is determined to be smaller than the diameter of each aperture in the second lens disks and provide a smaller viewing angle when each optical element in the second lens disks is disposed in the test window than when each aperture in the second lens disks is disposed in the test window.

2. The vision tester according to claim 1, wherein the aperture in the second auxiliary lens disk on a farther side from the examinee's eye has a diameter larger than the aperture in the first auxiliary lens disk on a closer side to the examinee's eye.

3. The vision tester according to claim 1, wherein each optical element in the first lens disks and each optical element in the second lens disks are 20 cm in diameter.

4. The vision tester according to claim 1, wherein each optical element in the first lens disks and each optical element in the second lens disks are 19 cm in effective diameter.

5. The vision tester according to claim 1, wherein the sphere lens disk comprises two lens disks each having one aperture and eleven sphere lenses.

6. The vision tester according to claim 1, wherein the cylinder lens disk comprises two lens disks each having one aperture and five cylinder lenses.

7. The vision tester according to claim 1, wherein the diameter of each optical element in the second lens disks is determined not to provide the viewing angle of the examinee's eye of 40° or more when each optical element in the second lens disks is disposed in the test window.

\* \* \* \* \*